(12) United States Patent
Krishnan et al.

(10) Patent No.: US 11,285,234 B2
(45) Date of Patent: Mar. 29, 2022

(54) EXHAUST AIR ODOR REMOVAL SYSTEM

(71) Applicant: Ruks Engineering Ltd., Brampton (CA)

(72) Inventors: Narayan Krishnan, Brampton (CA); Santanam Sridhar, Brampton (CA)

(73) Assignee: Ruks Engineering Ltd., Brampton (CA)

( * ) Notice: Subject to any disclaimer, the term of this patent is extended or adjusted under 35 U.S.C. 154(b) by 91 days.

(21) Appl. No.: 15/517,309

(22) PCT Filed: Oct. 6, 2014

(86) PCT No.: PCT/CA2014/050968
§ 371 (c)(1),
(2) Date: Apr. 6, 2017

(87) PCT Pub. No.: WO2016/054717
PCT Pub. Date: Apr. 14, 2016

(65) Prior Publication Data
US 2017/0246334 A1    Aug. 31, 2017

(51) Int. Cl.
*A61L 9/12* (2006.01)
*A61L 9/22* (2006.01)

(52) U.S. Cl.
CPC ................. *A61L 9/12* (2013.01); *A61L 9/22* (2013.01); *A61L 2209/14* (2013.01)

(58) Field of Classification Search
CPC ..................... A61L 9/12; A61L 9/22
See application file for complete search history.

(56) References Cited

U.S. PATENT DOCUMENTS

| 4,027,169 A * | 5/1977 | Lowther ............... H01S 3/092 422/186.16 |
| 4,124,021 A * | 11/1978 | Molitor ................ B23P 15/26 126/299 E |
| 4,765,803 A * | 8/1988 | Hirth .................... B01D 51/02 95/62 |
| 4,780,277 A | 10/1988 | Tanaka et al. |

(Continued)

FOREIGN PATENT DOCUMENTS

| GB | 2413377 | 10/2005 |
| WO | WO2007/061295 | 5/2007 |

*Primary Examiner* — Regina M Yoo
(74) *Attorney, Agent, or Firm* — McMillan LLP

(57) ABSTRACT

A system for neutralizing odors present in exhaust air extracted from a space via an exhaust air duct, the system including an air intake chamber; an air intake means for bringing environmental air into the air intake chamber and a corona chamber in air flow communication with the air intake chamber, and adapted to receive air from the air intake chamber. The corona chamber includes at least two spaced apart and perforated corona plates with perforated stainless steel mesh providing a dielectric medium into which an electrical spark voltage is provided to generate ozone from oxygen present in the environmental air to thereby transform the environmental air into ozone-rich air. A reaction chamber is also provided and adapted to receive the exhaust air and the ozone rich air allowing the mixing of the exhaust air and the ozone-rich air to thereby neutralize the odors before being discharged via an air outlet into the environment.

9 Claims, 2 Drawing Sheets

(56) References Cited

U.S. PATENT DOCUMENTS

| | | | | |
|---|---|---|---|---|
| 5,282,891 | A * | 2/1994 | Durham | B03C 3/455 |
| | | | | 96/75 |
| 5,525,310 | A * | 6/1996 | Decker | C01B 13/11 |
| | | | | 422/186.07 |
| 6,241,809 | B1 * | 6/2001 | Hopkins | B01D 45/06 |
| | | | | 55/DIG. 36 |
| 6,991,768 | B2 | 1/2006 | Keras et al. | |
| 7,252,807 | B2 * | 8/2007 | Hopkins | B01D 45/06 |
| | | | | 422/168 |
| 8,318,084 | B2 | 11/2012 | Johnson et al. | |
| 8,889,079 | B2 | 11/2014 | Zahedi | |
| 2002/0098109 | A1 * | 7/2002 | Nelson | A61L 2/10 |
| | | | | 422/5 |
| 2002/0182125 | A1 * | 12/2002 | Hopkins | B01D 45/06 |
| | | | | 422/168 |
| 2003/0108460 | A1 | 6/2003 | Andreev et al. | |
| 2005/0175498 | A1 * | 8/2005 | Nelson | A61L 2/10 |
| | | | | 422/4 |
| 2005/0214181 | A1 * | 9/2005 | Kaneko | B01J 19/088 |
| | | | | 422/186.04 |
| 2011/0111691 | A1 * | 5/2011 | Kagawa | A61L 9/22 |
| | | | | 454/251 |

\* cited by examiner

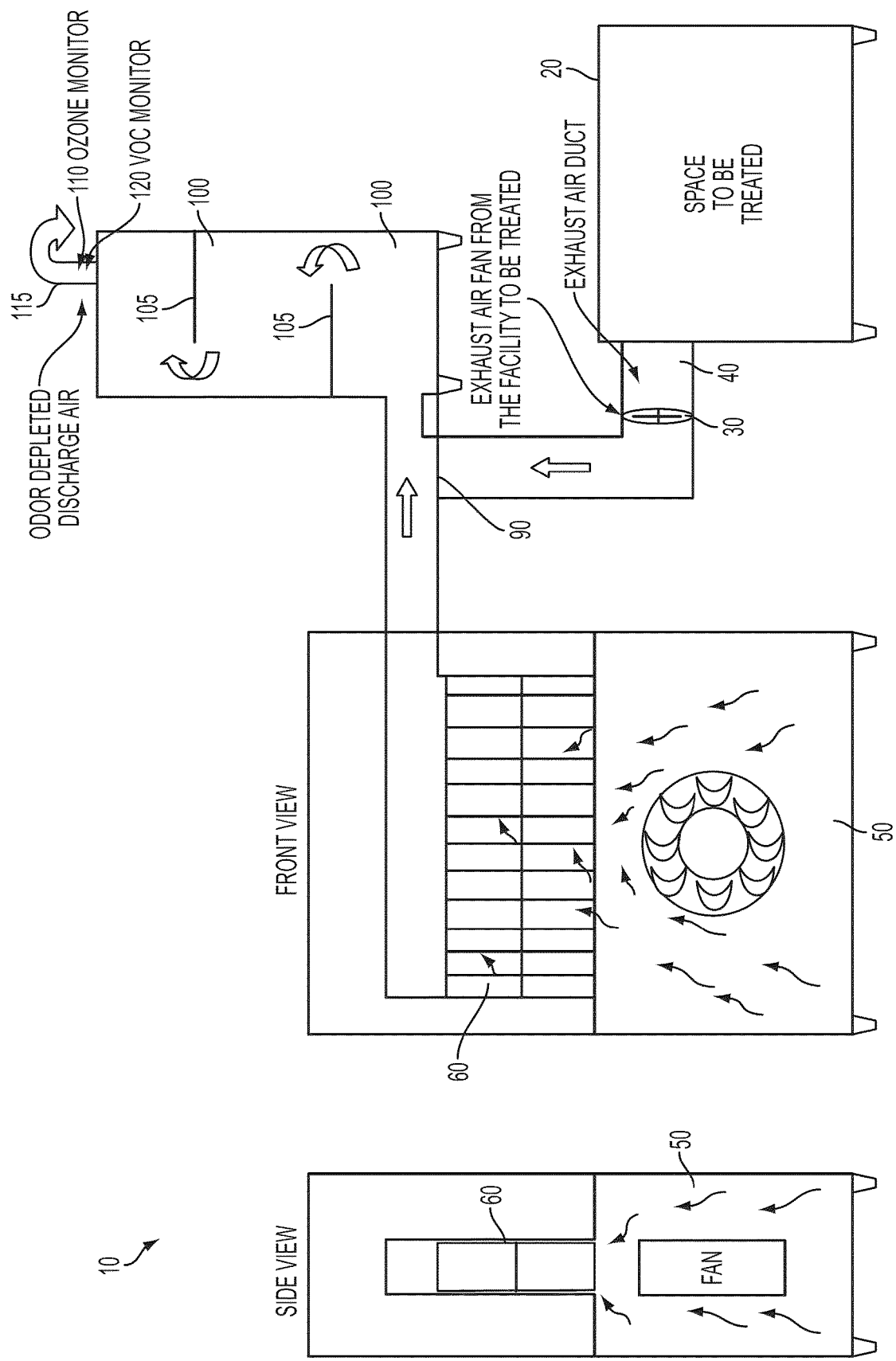

EXHAUST AIR ODOR REMOVAL SYSTEM

FIELD OF THE INVENTION

The invention relates to exhaust air odor removal systems, and in particular to the removal or elimination of odors from exhaust air generated by kitchen hoods, commercial, industrial or other equipment.

BACKGROUND OF THE INVENTION

Exhaust air is generally defined as air released from various types of kitchen hoods, commercial, industrial or other equipment following certain industrial, or other, processes. In many applications, exhaust air contains undesirable odors detectable in the environment into which the exhaust air is released. The odor in exhaust air can be caused by organic elements within the exhaust air that results from the processing which occurs in processing of materials at facilities such as sewage and waste water treatment plants, lift wells and headworks stations, food processing plants, animal houses, pharmaceutical and medical research facilities, kitchen exhaust air hoods, garbage holding and compacting facilities, and others. Industrial/commercial kitchens is another application where such odors are undesirable, particularly in crowded cities where the exhaust air may be discharged into areas surrounding a building which are heavily trafficked by pedestrians, or homes or offices, or may be in proximity to air intake system of Air Handling Units of other users or facilities.

Various prior art solutions aimed at the odor problem in exhaust air have been implanted, to mixed degrees of success. It is common to use carbon and/or chemical filters, in combination with wet scrubbers to remove odors. The performance ability depends on the efficiency of these filters, and more importantly on the frequency of change of the filter media. This adds significant operating costs both in replacing the filter and in monitoring when a filter is in need of replacement. Often times, the filters are located in difficult to access places and changes require cost significant technician man hours. In addition, performance is not uniform over the lifespan of the filter. A new filter has a high degree of odor absorption/adsorption, but the performance of the filter deteriorates as the filter ages until the filter is in need of replacement. Over the lifecycle of the processing equipment, the cost of replacement filters is fairly high, and can be several times higher than the capital cost of the equipment itself, when considering technician costs, system downtime and the actual cost of the filter itself.

In addition, filters are typically installed in banks to provide sufficient capacity in larger operations. These filter banks impose high resistance to air flow, and thus larger fan motors are needed to properly discharge the exhaust air. This also results in additional capital costs and operating costs. Increased power consumption adds to environmental concerns, increases carbon footprint, and use of fossil fuel.

Wet scrubbers consume large amounts of water as part of the circulated water is evaporated and needs to be replaced. This is environmentally undesirable, particularly in environments where water shortages are hot button issues. Other environment issues include the need to dispose of filters and chemicals used in chemical filters and wet scrubbers.

Accordingly, there is a need in the prior art for improved odor removal of exhaust air which mitigates at least one of the aforementioned problems with the prior art.

SUMMARY OF THE INVENTION

According to one embodiment of the invention, there is provided a system for neutralizing odors present in exhaust air extracted from a space via an exhaust air duct, the system including an air intake chamber; an air intake means for bringing environmental air into the air intake chamber; a corona chamber in air flow communication with the air intake chamber, and adapted to receive air from the air intake chamber; the corona chamber including at least two spaced apart corona plates providing a dielectric medium into which an electrical is provided to generate ozone from oxygen present in the environmental air to thereby transform the environmental air into ozone-rich air; a reaction chamber adapted to receive the exhaust air and the ozone rich air; the reaction chamber sized and otherwise dimensioned to permit sufficient time for odor-causing elements in the exhaust air to react with ozone in the ozone-rich air to thereby neutralize the odors; and an air outlet connected to the reaction chamber through which odor-neutralized air is discharged into the environment.

In one aspect of the invention, each corona plate comprises an electrically inert substrate frame supporting a perforated material capable of transmitting an electrical spark voltage.

In another aspect of the invention, the electrically inert substrate comprises an alumina substrate.

In another aspect of the invention, the perforated material comprises a stainless steel mesh.

In another aspect of the invention, there is provided at least one contactor between each corona plate; the at least one contactor attached to a power source and adapted to transmit a spark voltage to each corona plate.

In another aspect of the invention, the at least one contactor is a stainless steel contactor transmitting a single phase voltage of between 6,000 and 8,000 VAC to generate the spark voltage.

In another aspect of the invention, the at least two corona plates are a plurality of corona plates, spaced approximately ¾" apart.

In another aspect of the invention, the exhaust air and the ozone rich air are merged into a common flow path prior to entry into the reaction chamber.

In another aspect of the invention, the exhaust air and the ozone-rich air are received in reaction chamber by separate flow paths.

In another aspect of the invention, the reaction chamber includes at least one baffle.

In another aspect of the invention, the reaction chamber includes a plurality of baffles positioned on alternating sides of the reaction chamber.

In another aspect of the invention, there is provided an ozone monitor positioned proximate the air outlet for detecting ozone levels in the discharged air.

In another aspect of the invention, the ozone monitor is in communication with a controller configured to adjust the levels of ozone production in the corona chamber by adjusting the voltage of the electric spark voltage in response to higher than acceptable levels of ozone in the discharged air.

In another aspect of the invention, there is provided a volatile organic compound monitor positioned proximate the air outlet for detecting levels of volatile organic compounds in the discharged air.

In another aspect of the invention, the volatile organic compound monitor is in communication with a controller configured to adjust the levels of ozone production in the corona chamber for adjusting the voltage of the electric spark voltage in response to higher than acceptable levels of volatile organic compounds in the discharged air.

BRIEF DESCRIPTION OF THE DRAWINGS

FIG. 1 shows a side view of an exhaust air odor removal system according to one embodiment of the invention FIG.

Figure 3:
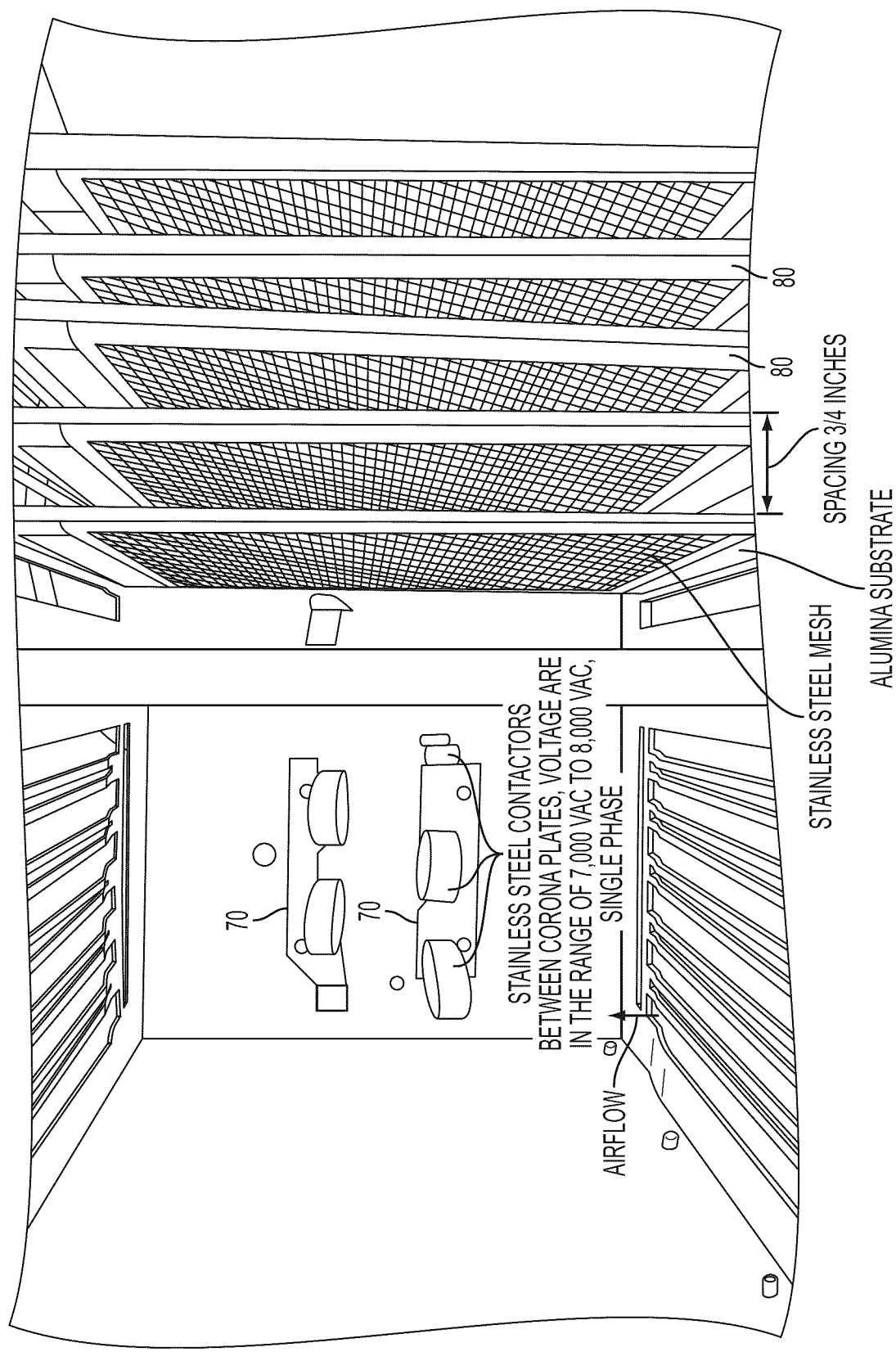

2 shows a front view of an exhaust air odor removal system according the same embodiment of the invention as in FIG. 1.

FIG. 3 is a detail view of the interior of a corona chamber according to an embodiment of the invention.

DETAILED DESCRIPTION

The invention as herein described aims to provide for an odor removal system which largely avoids the necessity of using replacement consumable items, such as carbon filters, and chemical scrubbers. In addition, it is also preferred that the increase in static pressure on the fan in the exhaust air removal system of prior art filter-based systems can be avoided, as is almost inevitably the case with the use of carbon filter banks as is typical in the prior art. One way to address these objectives is to use a system in which the odor removal properties of ozone can be utilized within an exhaust air removal system. The odor removal capabilities of ozone are widely know and thus are not discussed in further detail, however, a system which allows for ozone to be injected or otherwise mixed with an exiting stream of exhaust air is believed to be heretofore unknown in the prior art.

In this regard, and turning now to FIGS. 1 and 2, there is shown an exhaust air odor removal system 10 according to one embodiment of the invention. The odor removal system 10 is integrated into the air flow path of a space to be treated 20. The space to be treated 20 may be a commercial kitchen hood or room, a sewage plant, or any other space through which exhaust air is extracted. Typically, an exhaust air fan 30 draws odor-filled air out of the space to be treated 20 via an exhaust air duct 40. In the prior art, this exhaust duct is either in flow communication with a carbon filter bank or is discharged completely into the environment. The system of the invention is designed to provide a flow of oxidized air to mix with the discharge air leaving the space to be treated, and to provide for sufficient mixing of the flow of oxidized air with the odor-filled air to thereby remove all or substantially all odors prior to discharging air into the environment.

The system includes an ambient air intake chamber 50 having a fan adapted to draw in ambient air at prevailing ambient conditions. This type of fan is generally known in the HVAC arts, and could be a backward curved, non-overloading type fan. Although, the invention contemplates other means for drawing air into the ambient air intake chamber 50. The purpose of the chamber 50 is to draw in ambient, or atmospheric, air and such that a buildup of air within the chamber 50 results in an increase in pressure of the air in the chamber 50.

Upstream, and in direct flow communication with the air intake chamber 50 is a corona chamber 60, a detailed view of which is shown in FIG. 3. The left half of FIG. 3 is shown with corona plates removed, to properly illustrate elements behind or between the corona plates 80, which are shown on the right side of FIG. 3. The corona chamber 60 preferably includes a hilly welded section having a plurality of double sided plate-type coronas, referred to herein as corona plates 80, stacked alongside one another in one or more rows in height. The corona plates 80 are embedded between two perforated, or otherwise adapted to permit air flow through the plates. Between each of the corona plates are one or more stainless steel contactors providing a voltage in the range of approximately 7000 VAC to 8000 VAC. A power supply is used to produce an electrical voltage discharge at the contactors and across the air gap between each corona plate 80. Each of the corona plates 80 includes a dielectric, which in the illustrated embodiment is an alumina substrate holding a stainless steel mesh, although other dielectrics are contemplated. The dielectric is used to diffuse the discharge from the spark voltage created by the stainless steel contactors 70 across the length and width of the corona plates 80. The oxygen molecules present in the air passing through the air gap are exposed to the electrical discharge, and are split into ozone. This reaction is known in the ozone generation arts, and the description provided above is to facilitate in the implementation in the novel manner as taught by the invention.

Preferably, the gap between each of the corona plates 80 is sufficient so as not to allow sparking between adjacent plates, but close enough to use the length of the slot available as efficiently as possible. The corona plates 80 consist of an alumina substrate embedded between a stainless steel mesh on either side. The thickness of the corona plates 80 is chosen such that an efficient dielectric medium can be provided without allowing direct electrical charge voltage between the conductors. In an exemplary installation of a commercial kitchen, the spacing between the corona plates 80 is approximately ¾ inch or 1.9 cm.

The corona plates 80 as herein described are selected as the ozone producing device rather than more typical prior art corona annular tube devices. The purpose of this is to avoid the need to use compressed air or oxygen to flow over-through the corona plates/annular tubes, which provides an advantage in not requiring an air compressor, molecular sieves, which are prone to frequent failure or servicing requirements. Other methods of generating ozone require molecular sieves, however these too require frequent replacement and are therefore undesirable. The only inputs into the system of the invention are the ambient air from the surrounding environment and the electrical requirements to generate the corona spark voltage, along with routine operating power requirements.

The corona chamber 60 is completely sealed to the environment, for example by being fully welded so as to avoid any outside leak of ozone. Downstream from an exit of the corona chamber 60, the ozone-rich air is mixed with air leaving the exhaust duct 40 by merging their flow paths, as illustrated at intersection 90. The merged flow path then follows in a reaction chamber 100. Optionally, the ozone-rich air leaving the corona chamber 60 and the odorous air extracted from the space to be treated 20 can be fed directly and separately into the reaction chamber 100.

The reaction chamber 100 is sized and otherwise dimensioned such that its volume permits adequate reaction time between the odor-filled air withdrawn from the space being treated 20 and the ozone-rich air leaving the corona chamber 60. As reacted air is discharged to the external environment upon leaving the reaction chamber 100, the only constraints on the size of the reaction chamber 100 are based on the physical space available at the site in which the invention is being installed. Preferably, the reaction chamber is provided with one or more baffles 105 to extend the path of the air traveled through the reaction chamber such that the odor-filled and ozone-rich air streams are forced into close contact and further reaction time and space is permitted. With the appropriate reaction time and reaction volume, near total oxidation occurs as the air exits the reaction chamber 100 and into the surrounding environment. The reaction time and chamber volume can readily be determined based on the size of the space being treated. The invention is not limited to particular sizes for the reaction chamber, and over-sizing the reaction chamber provided the practical space is available is one way to ensure a complete reaction of the ozone-rich air with the odor-filled air to thereby eliminate or neutralize the odor.

An ozone sensor and controller 110 may be installed proximate an outlet 115 of the reaction chamber 100 to deactivate or regulate ozone production, for example by providing or cutting off the voltage applied to the corona plates, in the event that the concentration to ozone in the released air exceeds regulatory mandated levels, should such mandated levels exist in the environment in which the invention is implemented. An optionally, there is also provided a volatile organic compound sensor for specific odorous gases that need to be removed. If it is detected that a particular gas is present in unacceptable levels at the exit of the reaction chamber 100, the level of ozone production can be increased by increasing the voltage provided to the corona plates.

Optionally, there is also provided a hydrogen sulfide sensor for hydrogen sulfide that needs to be released. If it is detected that hydrogen sulfide is present in unacceptable level at exit of the reaction chamber 100, the level of ozone production can be increased by increasing the voltage provided to the corona plates.

While the description provided above is generic to various sizes of spaces from which odors are desired to be removed, an exemplary embodiment has been implemented successfully by the applicant. In this exemplary implementation of a typical sized commercial kitchen producing about 10,000 to 14,000 Cfm of exhaust air, the installation is provided with approximately 60 corona plates having an applied voltage of between 7000 V to 8000 V. These ranges are provided to accommodate the sub variation seen in kitchen exhaust air depending on the type of cuisine and levels of odorous elements in the exhaust air. The corona plates used in this example comprised multiple numbers of 96% alumina substrate with a thickness of 35 thou and an embedded stainless steel mesh #10 size. The plates were spaced approximately ¾" apart, and applied with a voltage of 6,000 to 8,000 V. This implementation resulted in the removal of all unaided detectable odors in test kitchens emitting different types of odors.

While the aforementioned example is provided to show one successful implementation, the invention is not to be considered limited by this example. Different types of spaces from which odors are removed, as listed earlier, will have different parameters, dimensions and operating conditions of implementation.

As will also be apparent to one skilled in the art, the invention can readily be retrofitted into existing installations and odorous air treated without the use of carbon filters, chemical scrubbers, or other disposable parts. Furthermore, no modifications are required of any equipment already withdrawing odor-filled air from a space being treated.

Various modifications and alterations may be possible to the various embodiments as herein described that would be appreciated by a person skilled in the art having regard to this description. For example, in another aspect of the invention, there is provided a hydrogen sulfide monitor positioned proximate the air outlet for detecting level of hydrogen sulfide in the discharged air. For example, in another aspect of the invention, the hydrogen sulfide monitor is in communication with a controller to adjust the levels of ozone production in the corona chamber for adjusting the voltage in response to higher than acceptable levels of hydrogen sulfide in the discharged air. In another aspect of the invention, there is provided a fan chamber with a backward inclined, non overloading fan. This draws ambient air through a particle filter and fills the discharge chamber. Uniformly cut opening at the top of the chamber facilitate even distribution of air through the corona module to optimize ozone output from all the corona plates regardless of their physical location in the corona chamber. Due to significant variation of site system static pressure in different installations, in this aspect of invention, there is provided a non overloading fan to ensure operation with varying site imposed static pressure constraints, without resulting in burnout of the fan motor. In another aspect of the invention, there is provided set of transformers in the electrical enclosure. To minimize loss of operational capacity, each transformer operates a set of corona plates dedicated to the specific transformer. In the event of failure of one transformer, only one set of corona plates would be out of operation, while others would continue to function. In another aspect of the invention, the transformer uses Cross Ferro magnetic core which is impervious to failure and loss of operational safety even if short circuit occurs on the secondary side of the transformer or the corona chamber. In another aspect of the invention, this transformer is fully encapsulated in an 18 G dome shaped single piece die cast enclosure. This makes the transformer impervious to exposure to moisture, rain water and snow, and renders it suitable for operation in wet outdoor conditions, in addition to indoor conditions. In another aspect of the invention, output of high voltage on the secondary of the transformer is protected with porcelain insulators embedded in the metallic enclosure of the transformer. A stainless steel rod that runs through the embedded porcelain premits the high secondary voltage to be applied to the corona plates. In another aspect of the invention, delivery of high voltage from transformer housed in electrical enclosure to corona cells housed in corona enclosure, is by cables with silicon insulation to render it ozone and UV resistant, crack and surface failure resistant if bent with short radius, and resistant to fire. In this aspect of the invention, combination of above features renders the invention extremely safe for operation, and against moisture and fire. In another aspect of the invention, output of voltage and power from transformer is modulated depending on the extent of requirement of ozone based on the extent of presence of VOC, odor or hydrogen sulfide in the air exhausted to the atmosphere. This conserves electrical power, leading to savings in operating cost, contributing to environmental benefits, reduction of carbon foot print, and reduces use of fossil fuel. In another aspect of this invention, there is provided a removable panel with glass or plexi glass see through plate. This enables user to observe corona cells in completely safe manner while the equipment is in operation. This aspect of the invention renders it possible to limit maintenance to only if the corona cells are contaminated with dust and particulate. This aspect of the invention helps operation of the invention with practically no maintenance, or reduces maintenance to near zero as long as air filter is changed periodically to prevent dust infusion on the corona plates. Above aspects of the invention, help operate the equipment with virtually no periodic maintenance. This results in enormous savings in labor cost for maintenance, reduces or eliminates down time for periodic maintenance, helps achieve higher utilization of the equipment, and results in savings in operating cost.

The scope of the claims should not be limited by the preferred embodiments set forth in the examples, but should be given the broadest interpretation consistent with the description as a whole.

We claim:

1. A system for neutralizing a plurality of odors present in exhaust air extracted from a space via an exhaust air duct, the system comprising:
   an air intake chamber;
   an air intake means for bringing environmental air into said air intake chamber;
   a corona chamber in air flow communication with said air intake chamber, and adapted to receive air from said air intake chamber, and having an exit;
   said corona chamber including a plurality of spaced apart corona plates into which an electrical spark voltage is provided to generate ozone from oxygen present in the environmental air to thereby transform the environmental air into ozone-rich air, each of the plurality of spaced apart corona plates comprising an alumina substrate and a stainless steel mesh;
   a contactor disposed between the plurality of spaced apart corona plates, the contactor adapted to be attached to a power source to transmit the electrical spark voltage across an air gap between said plurality of spaced apart corona plates;
   an exhaust inlet positioned downstream of the corona chamber and in fluid communication with an exhaust air duct for introducing the exhaust air to the ozone-rich air;
   a reaction chamber adapted to receive a mixture of the exhaust air and the ozone-rich air, said reaction chamber sized and otherwise dimensioned to permit sufficient time for odor-causing elements in the exhaust air to react with ozone in the ozone-rich air to thereby neutralize the plurality of odors; and
   an air outlet connected to said reaction chamber through which odor-neutralized air is discharged;
   wherein said reaction chamber includes a plurality of baffles positioned on alternating sides of said reaction chamber.

2. The system according to claim 1, further comprising the power source, wherein said contactor is attached to the power source and transmitting the electrical spark voltage to each of said plurality of spaced apart corona plates.

3. The system according to claim 2, wherein said contactor comprises a stainless steel contactor transmitting a single phase voltage of between 6,000 and 8,000 VAC.

4. The system according to claim 1, wherein said plurality of spaced apart corona plates are spaced approximately ¾" apart.

5. The system according to claim 1, wherein the exhaust air and the ozone-rich air are merged into a common flow path prior to entry into said reaction chamber.

6. The system according to claim 1, further comprising an ozone monitor positioned proximate said air outlet for detecting ozone levels in the discharged air.

7. The system according to claim 6, wherein said ozone monitor is in communication with a controller configured to adjust a level of ozone production in said corona chamber for adjusting the voltage of said electric spark voltage in response to higher than acceptable levels of ozone in said discharged air.

8. The system according to claim 1, further comprising a volatile organic compound monitor positioned proximate said air outlet for detecting levels of volatile organic compounds in the discharged air.

9. The system according to claim 8, wherein said volatile organic compound monitor is in communication with a controller configured to adjust a level of ozone production in said corona chamber for adjusting the voltage of said electric spark voltage in response to higher than acceptable levels of volatile organic compounds in the discharged air.

* * * * *